United States Patent
Mezei et al.

(10) Patent No.: US 8,097,616 B2
(45) Date of Patent: Jan. 17, 2012

(54) PROCESS FOR PREPARATION OF HIGH-PURITY MELOXICAM AND MELOXICAM POTASSIUM SALT

(75) Inventors: Tibor Mezei, Budapest (HU); Gyula Simig, Budapest (HU); Enikó Molnár, Érd (HU); Gyula Lukács, Budapest (HU); Márta Porcs-Makkay, Pomáz (HU); Balázs Volk, Budapest (HU); Valéria Hofmanné Fekete, Budapest (HU); Kálmán Nagy, Budapest (HU); Norbert Mesterházy, Szombathely (HU); György Krasznai, Budapest (HU); Györgyi Vereczkeyné Donáth, Budapest (HU); Gyuláné Körtvélyessy, Budapest (HU); Éva Pécsi, Budapest (HU)

(73) Assignee: Egis Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 639 days.

(21) Appl. No.: 11/793,548

(22) PCT Filed: Dec. 16, 2005

(86) PCT No.: PCT/HU2005/000136
§ 371 (c)(1),
(2), (4) Date: Jan. 7, 2009

(87) PCT Pub. No.: WO2006/064298
PCT Pub. Date: Jun. 22, 2006

(65) Prior Publication Data
US 2009/0215757 A1    Aug. 27, 2009

(30) Foreign Application Priority Data

Dec. 18, 2004  (HU) ................................... P0402634

(51) Int. Cl.
*C07D 417/12* (2006.01)
*A61K 31/427* (2006.01)
*A61P 29/00* (2006.01)

(52) U.S. Cl. ...................................... 514/226.5; 544/49
(58) Field of Classification Search ................... 544/49; 514/226.5
See application file for complete search history.

(56) References Cited

U.S. PATENT DOCUMENTS

| 4,233,299 A * | 11/1980 | Trummlitz et al. ........ 514/226.5 |
| 6,869,948 B1 | 3/2005 | Bock et al. ................. 514/226.5 |
| 7,671,197 B2 | 3/2010 | Vigano' et al. |
| 2003/0109701 A1 | 6/2003 | Coppi et al. .................... 544/49 |
| 2004/0180092 A1 | 9/2004 | Henke et al. |
| 2006/0116514 A1 | 6/2006 | Vigano et al. ................... 544/49 |

FOREIGN PATENT DOCUMENTS

EP   1 645 559   12/2006

OTHER PUBLICATIONS

Peter Luger et al; Structure and physicochemical properties . . . ; European Jour. of Pharm. Sciences 4 (1996) 175-187.
Edward Lazer et al; Effect of structural modification of Enol . . . ; J. Med. Chem. 1997, 40, 980-989—XP-002379086.
E.S. Lazer et al: "Effect of Structural Modification of Enol-Carboxamide Type Nonsteroidal Antiinflammatory Drugs on COX-2/COX-1 Selectivity", Journal of Medicinal Chemistry, vol. 40, 1997, pp. 980-989, tables 1,2.

* cited by examiner

*Primary Examiner* — Kahsay T Habte
(74) *Attorney, Agent, or Firm* — Jonathan Myers; Andrew Wilford

(57) ABSTRACT

The invention provides a process for the preparation of high purity meloxicam of the Formula (II). The meloxicam raw product is reacted with the solution of potassium hydroxide or potassium carbonate, whereby high purity meloxicam potassium sait monohydrate is produced. Said sait is subsequently treated with mineral or organic acid to yield high-purity meloxicam.

6 Claims, No Drawings

PROCESS FOR PREPARATION OF HIGH-PURITY MELOXICAM AND MELOXICAM POTASSIUM SALT

CROSS REFERENCE TO RELATED APPLICATIONS

This application is the US National Phase of PCT Application PCT/HU2005/00136 filed 16 Dec. 2006 with a claim to the priority of Hungarian National Patent Application HU PO402634 filed 18 Dec. 2004.

FIELD OF THE INVENTION

The present invention relates to a process for the preparation of 4-hydroxy-2-methyl-N-(5-methyl-2-thiazolyl)-2H-1,2-benzothiazine-3-carboxamide-1,1-dioxide of the Formula (II),

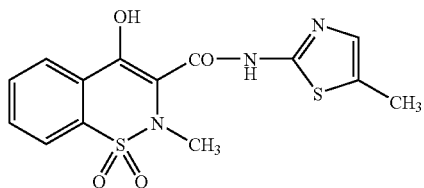

also known by the International Nonproprietary Name (INN) meloxicam and its potassium salt monohydrate of the Formula (I)

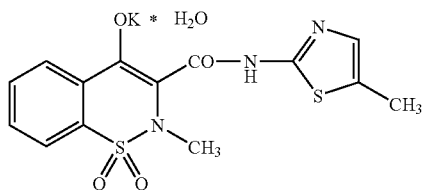

in high purity.

TECHNICAL BACKGROUND OF THE INVENTION

Meloxicam belongs to the group of non-steroidal antiinflammatory drugs. It exerts its pharmacological effect by the inhibition of the cyclooxygenase (COX) enzyme system, which has significant role in the development of inflammatory processes. The medicinal importance of meloxicam resides in the fact that meloxicam selectively inhibits the COX-2 enzyme. This phenomenon results in less adverse effects during the medication period. It was found that the probability of the development of kidney-related or gastrointestinal adverse effects is significantly lower during the treatment using meloxicam than in those cases, when different, non-selective COX-inhibitors were administered.

Processes for the preparation of meloxicam have been disclosed in European Patent No. 2482. According to the first process, an activated form of 4-hydroxy-2-methyl-2H-1,2-benzothiazine-3-carboxylic acid of the Formula (III),

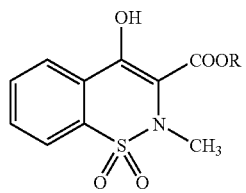

such as its methyl-, ethyl- or isopropyl ester (wherein the meaning of the R group in the Formula (III) is methyl, ethyl or isopropyl, respectively) is reacted with 2-amino-5-methyl-thiazole of the Formula (IV)

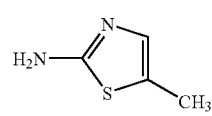

at high temperature. During this reaction, by-products with similar chemical structure to meloxicam and some tar are also formed, therefore further purification of the raw product is required. Solvents most often used for the recrystallization of raw meloxicam are dichloroethane and dichloromethane. The above mentioned process has the disadvantage that toxic and costly solvents are used, which are harmful to the environment as well. During the subsequent drying, it must be assured that the residual solvent concentration in the finished active ingredient should not exceed a threshold concentration set by health authorities and pharmacopoeias. At the drying temperature, thermal decomposition of the active ingredient also takes place. Use of halogenated organic solvents requires extensive analytical testing, because the residual solvent concentration must be determined in costly analytical measurements.

In the second known process, the nitrogen atom of the 2H-1,2-benzothiazine ring is methylated using either the very expensive methyl jodide or the extremely toxic dimethyl sulfate. Due to its low yield and high production costs, this process is not used on an industrial scale.

It was found that when using the above mentioned processes, the by-product 4-hydroxy-2-methyl-N-alkyl-(5-methyl-2-thiazolyl)-2H-1,2-benzothiazine-3-carboxamide-1,1-dioxide of the Formula (V),

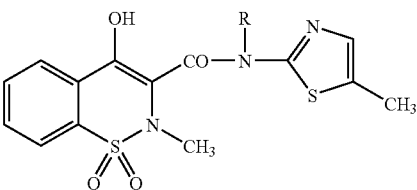

wherein the alkyl group corresponds identical to the R group in the starting compound of the Formula (III), i.e. methyl, ethyl or isopropyl, is formed in an amount of 1-20% by weight. Compounds of the Formula (V) are crystalline compounds poorly soluble in organic solvents and having their melting point above 250° C. Impurities of the Formula (V) can be removed partly by filtering the hot solution of meloxicam crude product. However, a dissolved portion of the compounds of Formula (V) amounting to a few tenth percent crystallizes together with meloxicam upon cooling, therefore compounds of the Formula (V) appear in the final pharmaceutical active ingredient as impurity. It was observed that the compounds of the Formula (V) are produced in the largest quantity (10-20% by weight), if the compound of the Formula (III) is used as starting material wherein R is methyl. The smallest amount of the compound of Formula (V) is produced in the case when R is isopropyl in the starting compound of the Formula (III). According to the specifications of the pharmacopoeias, threshold concentration of the compounds of the Formula (V) is 0.1% by weight, which could be achieved only after recrystallizing the crude product several times from dichloromethane.

United States Patent Application No. 20030109701 discloses processes for the preparation of several meloxicam polymorph forms by dissolving meloxicam in sodium-hydroxide solution prepared in water or in the mixture of water and an organic solvent, subsequently acidifying the solution of meloxicam sodium salt, thus setting meloxicam free from its sodium salt. In this way, different crystalline modifications of meloxicam are obtained, depending upon the conditions used during dissolution and precipitation. Subsequently, the polymorph form obtained in the above described process is converted into the pharmaceutically acceptable polymorph I form.

SUMMARY OF THE INVENTION

The objective of our research has been to develop a process for the preparation of high purity meloxicam suitable as pharmaceutical active ingredient and said high purity meloxicam being essentially free of 4-hydroxy-2-methyl-N-alkyl(5-methyl-2-thiazolyl)-2H-1,2-benzothiazine-3-carboxamide-1,1-dioxide impurity of the Formula (V), wherein the meaning of alkyl is methyl, ethyl or isopropyl.

The above objective is solved according to the present invention.

Surprisingly, it has been found that meloxicam potassium salt monohydrate of the Formula (I) can be crystallized from aqueous solution in exceptionally high purity, thus allowing the purification of raw meloxicam.

According to an aspect of the present invention, there is provided a process for the preparation of 4-hydroxy-2-methyl-N-(5-methyl-2-thiazolyl)-2H-1,2-benzothiazine-3-carboxamide-1,1-dioxide (meloxicam) of the Formula (II) of high purity, which comprises
  (a) dissolving meloxicam potassium salt monohydrate of the Formula (I) in water or in the mixture of water and an organic solvent, removing insoluble impurities and treating the resulting solution with an organic or inorganic acid, and crystallizing meloxicam; or
  (b) transforming meloxicam raw product into crystalline meloxicam potassium salt monohydrate of the Formula (I), dissolving said meloxicam potassium salt monohydrate of the Formula (I) in water or in a mixture of water and an organic solvent, removing insoluble impurities and treating the dissolved potassium salt of meloxicam with an organic or inorganic acid, followed by crystallization meloxicam of the Formula (II); or
  (c) reacting a compound of the general Formula (III), wherein R is methyl, ethyl or isopropyl with 2-amino-5-methyl-thiazole of the Formula (IV), transforming the resulting meloxicam of the Formula (II) into its potassium salt, separating insoluble impurities from aqueous or aqueous-organic solution of said meloxicam potassium salt, treating said solution with an organic or inorganic acid and crystallizing meloxicam.

According to a further aspect of our invention, there is provided a process for the preparation of meloxicam potassium salt of the Formula (I), by reacting meloxicam of the Formula (II) with potassium hydroxide or potassium carbonate dissolved in water or in the mixture of water and an organic solvent and if desired, crystallizing the meloxicam potassium salt monohydrate of the compound of the Formula (I) thus formed.

In the above mentioned process directed to the preparation of meloxicam potassium salt of the Formula (I) or monohydrate thereof, the molar amount of potassium hydroxide or potassium carbonate is 1-10 molar equivalent, preferably 4-5 molar equivalent of the molar amount of meloxicam.

If desired, any of the processes can be performed in water or in the mixture of water and an organic solvent. As organic solvent, an alcohol containing 1-4 carbon atoms, for example, methanol, ethanol or isopropanol, preferably ethanol can be used.

In the above mentioned process variants a) to c), meloxicam of the Formula (II) is set free from its potassium salt dissolved in water or in the mixture of the water and an organic solvent by treatment with an inorganic or an organic acid. Said acidic treatment is carried out by mixing the solution of meloxicam potassium salt of the Formula (I) with concentrated acid or an aqueous solution thereof. Suitable acids include any mineral or organic acids, for example, sulphuric acid, hydrochloric acid, phosphoric acid, tartaric acid, acetic acid.

Acidic treatment can be preferably carried out under the control of the acidity (pH value) of the solution of meloxicam potassium salt of the Formula (I). The acidic treatment is continued until pH 3 to 6, preferably until pH 6 is reached.

According to a further aspect of the present invention, there is provided 4-hydroxy-2-methyl-N-(5-methyl-2-thiazolyl)-2H-1,2-benzothiazine-3-carboxamide-1,1-dioxide (meloxicam) of the Formula (II) essentially free from 4-hydroxy-2-methyl-N-alkyl-(5-methyl-2-thiazolyl)-2H-1,2-benzothiazine-3-carboxamide-1,1-dioxide of the Formula (V), wherein the R alkyl group of the Formula (V) is methyl, ethyl or isopropyl.

The invention further relates to meloxicam potassium salt monohydrate of the Formula (I), preferably in a purified state wherein said salt is essentially free from 4-hydroxy-2-methyl-N-alkyl-(5-methyl-2-thiazolyl)-2H-1,2-benzothiazine-3-carboxamide-1,1-dioxide of the Formula (V), wherein alkyl (Group R in the Formula (V)) is methyl, ethyl or isopropyl.

According to a still further aspect of the invention, there are provided pharmaceutical preparations comprising meloxicam potassium salt monohydrate of the Formula (I) as active ingredient and one or more pharmaceutically acceptable vehicle or auxiliary agent, preferably in a purified state wherein said salt is essentially free from 4-hydroxy-2-methyl-N-alkyl-(5-methyl-2-thiazolyl)-2H-1,2-benzothiazine-3-carboxamide-1,1-dioxide of the Formula (V), wherein alkyl (Group R in the Formula (V)) is methyl, ethyl or isopropyl.

The invention further relates to pharmaceutical preparations comprising high purity meloxicam of the Formula (II) as active ingredient and one or more pharmaceutically acceptable vehicle or auxiliary agent, wherein the active ingredient meloxicam is essentially free from 4-hydroxy-2-methyl-N-alkyl-(5-methyl-2-thiazolyl)-2H-1,2-benzothiazine-3-carboxamide-1,1-dioxide of the Formula (V), wherein alkyl (Group R in the Formula (V)) is methyl, ethyl or isopropyl.

DETAILED DESCRIPTION OF THE INVENTION

Organic acids and phenols form salt with metals, which are usually well soluble in water. This phenomenon is often exploited for the purification of said compounds by dissolving the product in alkaline-aqueous medium and removing the alkaline- and water-insoluble organic impurities by filtration or extraction with a suitable non-miscible solvent.

It is known according to the state of the art that potassium salts crystallize less easily and have greater solubility in water and in organic solvents, than sodium salts. Potassium salts can be hygroscopic, therefore said salts are preferably isolated from their solution in organic solvents.

The preparation of sodium salt of meloxicam was disclosed in Example 2 of European Patent No. 2482. The methanolic solution of meloxicam is mixed with approximately equimolar amount of sodium methylate, the reaction mixture is evaporated to dryness, the sodium salt is suspended in the mixture of acetone-ether and filtered.

United States Patent Application No. 20030109701 discloses the preparation of meloxicam sodium salt by dissolving meloxicam in aqueous-organic solution of sodium hydroxide.

Although according to the state of the art, among alkaline metal salts of meloxicam, the potassium salt is also mentioned, no disclosure is available for the preparation of the potassium salt of meloxicam in solid form and no data can be found with regard to its stability, solubility and purity. According to the state of the art, salts prepared from meloxicam and inorganic or organic bases are prepared exclusively with the purpose to increase the solubility of meloxicam.

According to the state of the art, there is no disclosure for the preparation of meloxicam in high purity form or its purification via its salt formed an with inorganic or organic base.

It has been found very surprisingly, that the meloxicam potassium salt of the Formula (I) can be isolated easily in especially pure monohydrate form from the solution of the raw product prepared with water or, if desired, with aqueous-organic solvents, even in the case when the impurity of the Formula (V) is present in the amount of approximately 20% by weight.

The advantage of the preparation of the potassium salt of the Formula (I) resides in the fat that in this way impurities of the Formula (V) as well as other alkaline-insoluble contaminants can be completely and very easily removed from the raw product.

Despite of the fact that the compounds of Formula (V) contain an aromatic hydroxy group, they do not form salt with alkali metals, therefore they are insoluble in alkaline aqueous solution and can be removed from the solution of meloxicam potassium salt by filtration. The small amount of impurity present on the surface of the solid crystalline meloxicam potassium salt monohydrate of the Formula (II), including the traces of the compounds of Formula (V) can be removed by simple washing with an appropriate solvent, since meloxicam potassium salt monohydrate of the Formula (I) is practically insoluble in organic solvents, for example, in ethylacetate.

According to a further aspect of the present invention, there is provided a process for the preparation of high purity, crystalline meloxicam potassium salt monohydrate of the Formula (I). In the first step, meloxicam is produced starting from the compound of the Formula (III), wherein the meaning of R is methyl, which is reacted with the compound of Formula (IV). In this process, a by-product of the Formula (V), wherein the meaning of R is methyl, is produced in an amount of 10-15% by weight. The raw product is dissolved in aqueous potassium hydroxide or potassium carbonate solution at the temperate of 50 to 60° C., the impurities insoluble in the alkaline-aqueous solvent are removed by filtration or centrifugation, the clear solution is cooled and the crystalline, high purity meloxicam potassium salt monohydrate of the Formula (I) is isolated by filtration or centrifugation.

According to a further aspect of the present invention, there is provided a process to transform meloxicam potassium salt monohydrate of the Formula (I) into high purity meloxicam. The meloxicam potassium salt monohydrate of the Formula (I) is dissolved in water or in a mixture of water and an organic solvent, the solution is filtered, the filtrate is acidified by aqueous acid solution and cooled. Subsequently the crystalline meloxicam is collected, washed and dried.

According to another aspect of the present invention, there is provided a process for the production of high purity meloxicam polymorf I form. The potassium salt of the Formula (I) is dissolved in water at a temperature between 50 and 60° C., the aqueous solution is filtered, and the yellow solution is acidified until pH 6 using concentrated acid solution, the solution is cooled and the precipitated crystalline meloxicam polymorph I form is isolated by centrifugation or filtration.

The advantage of the process according to the present invention resides in the fact that the only solvent used during the purification process is water, therefore it is not necessary to remove organic solvent residues from the product. At the acidity (pH value) given above, the product is almost insoluble in water, therefore the yield is almost quantitative. During the above described process, heat stress of the product and thermal decomposition thereof is minimal, which allows the production of high purity product. The above described process does not involve hazardous chemicals, therefore it is advantageous from the environmental viewpoint. The use of the above described process results in significant cost reduction as well.

The above inventive concept according to our invention can be applied more generally. Among esters of the Formula (III), the methyl ester is the cheapest and is produced on the greatest scale. However, said methyl ester of the Formula (III), wherein R is methyl, has received but limited attention during the production of meloxicam, because of the fact that the by-product of the Formula (V), wherein R is methyl, is produced during the amidation reaction in a significant amount, about 10-15% by weight, which could not be removed by crystallization. Using the process according to the present invention, contaminated raw products containing the above mentioned high amounts of the compound of the Formula (V), wherein R is methyl, can be purified. In this manner, it has become possible to use the cheaper methyl ester of the Formula (III), wherein R is methyl, instead of the isopropyl ester of Formula (III), wherein R is isopropyl.

The preparation of the raw meloxicam of the Formula (II) is carried out according to state of the art by reacting an ester of the Formula (III), wherein R is methyl, ethyl or isopropyl and 2-amino-5-methyl-thiazole of the Formula (IV) in solvents having high boiling point, for example, in chloro-benzene, decaline or xylene, preferably, in xylene. The reaction takes place at the boiling point of the reaction mixture, at the temperature between about 130 and about 170° C. The reaction time is usually 12-24 hours. Besides the product meloxicam, the reaction mixture contains a significant amount of the compound of the Formula (V) corresponding to the staring compound of the Formula (III) with respect to the R group and tar-like substance as well. If desired, the reaction can be carried out in presence of activated carbon to decrease the amount of tar. During the reaction, meloxicam and the by-product of the Formula (V) crystallizes and precipitates from the reaction mixture, and can be removed by filtration together with activated carbon, if present.

The raw meloxicam, which may contain activated carbon as well, is dissolved in a 20-50-fold weight amount of aqueous potassium hydroxide solution at a temperature between 50 and 80° C. under stirring. If desired, the dissolution rate of meloxicam can be increased by adding about 3-5 volume % of low molecular weight alcohol, for example, methanol, ethanol or isopropanol. The volume of the potassium hydroxide solution is determined taking into account the quality and quantity of the low molecular weight alcohol.

The aqueous-alkaline solvent dissolves meloxicam only. The compound of the Formula (V), which is insoluble in alkaline medium is filtered together with activated carbon, if present. The clear yellow filtrate is cooled while the precipitation of crystalline meloxicam potassium salt monohydrate of the Formula (I) takes place.

Crystallization of meloxicam potassium salt monohydrate can be enhanced by salting-out. To achieve salting-out effect, an amount of potassium hydroxide or potassium carbonate is added to the solution of meloxicam potassium salt as solid or as concentrated aqueous solution in excess to the equimolar amount required for salt formation. Total amount of potassium ions present in the solution according to the present invention can be between 1-10 molar equivalents, preferably 4-5 molar equivalents relative to the molar amount of meloxicam.

The solid crystalline meloxicam potassium salt monohydrate of the Formula (I) is isolated, the impurities present on the surface of the crystals are washed away using cold water or an organic solvent or a mixture of thereof, for example, using ethylacetate, ethanol, methanol, isopropanol as organic solvent.

According to our observations, using the process of the present invention, meloxicam potassium salt monohydrate can be obtained in high purity even in the unfavourable case when the reaction mixture contained 15-20% of the compound of the Formula (V) by weight.

According to the present invention, there is provided a process for the preparation of meloxicam polymorph I form of the Formula (II) in high purity, which comprises dissolving meloxicam potassium salt monohydrate of the Formula (I) in water or in the mixture of water and 1-20 volume % of a low molecular weight alcohol at a temperature between 50 and 100° C., preferably at a temperature between 60 and 70° C. The solvent preferably comprises 2-5 volume % ethanol in water.

The solution is filtered, and the clear yellow filtrate is acidified to pH 6 using a mineral or organic acid. For acidification, any mineral or organic acid, for example, hydrochloric acid, sulphuric acid or phosphoric acid, acetic acid, tartaric acid can be used. The crystalline meloxicam is filtered off and washed with water and ethanol.

According to a further aspect of the present invention, there are provided pharmaceutical preparations comprising meloxicam potassium salt monohydrate of the Formula (I) in admixture with one or more conventional carrier(s) or auxiliary agent(s), essentially free of the impurity of the Formula (V).

Another further aspect of the present invention relates to pharmaceutical preparations comprising meloxicam of the Formula (II) in admixture with one or more conventional carrier(s) or auxiliary agent(s), essentially free from the impurity of the Formula (v).

The pharmaceutical compositions according to the present invention contain generally 0.1-95% by weight, preferably 1-50% by weight, particularly 5-30% by weight active ingredient.

The pharmaceutical compositions of the present invention may be suitable for oral (e.g. powders, tablets, coated tablets, capsules, microcapsules, pills, solutions, suspensions or emulsions), parenteral (e.g. injection solutions for intravenous, intramuscular, subcutaneous or intraperitoneal use), rectal (e.g. suppositories) transdermal (e.g. plasters) or local (e.g. ointments or plasters) administration or for the application in form of implants. The solid, soft or liquid pharmaceutical compositions according to the invention may be produced by methods conventionally applied in the pharmaceutical industry.

The solid pharmaceutical compositions for oral administration containing the compound of the Formula (I) may comprise vehicles, fillers or carriers (such as lactose, glucose, starch, potassium phosphate, micro-crystalline cellulose), binding agents (such as gelatine, sorbite, polyvinyl pyrrolidone), disintegrants (such as croscarmelose, Na-carboxy-methyl cellulose, crospovidone), tabletting auxiliary agents (such as magnesium stearate, talc, polyethylene glycol, silicic acid, silicon dioxide) and surface-active agents (e.g. sodium lauryl sulfate).

The liquid compositions containing meloxicam potassium salt of the Formula (I) in dissolved form are known according to the state of the art. Liquid pharmaceutical preparations suitable for oral administration according to the present invention can be suspensions or emulsions. Such compositions may contain suspending agents (e.g. gelatine, carboxymethyl cellulose), emulsifiers (e.g. sorbitane monooleate, solvents (e.g. water, oils, glycerol, propylene glycol, ethanol), buffering agents (e.g. acetate, phosphate, citrate buffers) or preservatives (e.g. methyl-4-hydroxybenzoate).

Soft pharmaceutical compositions containing as active ingredient a compound of the general Formula (I) or a pharmaceutically acceptable acid addition salt thereof, such as suppositories, contain the active ingredient evenly dispersed in the basic material of the suppository (e.g. in polyethylene glycol or cocoa butter).

The pharmaceutical compositions according to the present invention can be prepared by known methods of the pharmaceutical industry. The active ingredient is admixed with pharmaceutically acceptable solid or liquid carriers and/or auxiliary agents and the mixture is brought to galenic form. The carriers and auxiliary agents together with the methods which can be used in the pharmaceutical industry are disclosed in the literature (Remington's Pharmaceutical Sciences, Edition 18, Mack Publishing Co., Easton, USA, 1990).

The pharmaceutical compositions according to the present invention contain generally a dosage unit.

Further details of the present invention are provided in the following examples without limiting the scope of protection to said examples.

EXAMPLE 1

4-hydroxy-2-methyl-N-(5-methyl-2-thiazolyl)-2H-1, 2-benzothiazine-3-carboxamide-1,1-dioxide potassium salt monohydrate (compound of the Formula I)

350 ml of xylene are transferred into an apparatus equipped with Marcusson head and provided with means for inert gas purging. Purging with argon is started and 35.0 g (130 mmol) 4-hydroxy-2-methyl-2H-1,2-benzothiazine-3-caboxylic acid methylester of the Formula (III) [wherein the meaning of R is methyl], 15.0 g (132 mmol) of 2-amino-5-methyl-thiazole of the Formula (IV) and 6.0 g of activated carbon are added during continuos stirring and argon purge.

The reaction mixture is heated for 24 hours using an oil bath at a temperature between 170 and 180° C. The heating is adjusted in a way that only a minimal amount of distillate (2-5 ml/hour) is produced in the head. Distillation of methanol is ceased by the end of the reaction.

The reaction mixture is cooled to 25° C., crude meloxicam containing carbon and approximately 12% of the impurity of Formula (V) are filtered off and washed on the filter with xylene and ethanol. The crude product containing carbon is stirred in 1200 ml of 0.5% aqueous potassium hydroxide solution at the temperature of 50° C. for one hour, carbon and the impurity of Formula (V) insoluble in the alkaline solution are filtered off and the clear yellow solution at 25° C. are added dropwise the solution of 30 g potassium hydroxide in 100 ml water. The potassium salt of meloxicam is precipitated in the form of yellow crystals which are easily separable by filtration. The crystal suspension is stirred for two hours at 10° C., filtered and washed with water.

Yield, 42.9 g [81.0%, calculated on the amount of the compound of Formula (III)]

Content (on the basis of potassium content): 99.5%
Water (Karl Fischer method): 4.6%
Melting point, 170-171° C.
Elemental analysis [$C_{14}H_{12}KN_3O_4S_2.H_2O$ (407.5)]:

| Calculated | C: 41.26 | H: 3.46 | N: 10.31 | S: 15.74 |
| Measured | C: 41.20 | H: 3.52 | N: 10.21 | S: 15.61 |

Purity (HPLC): 99.8%.
Thermogravimetry: the product loses 4.75% water at 175-245° C.

EXAMPLE 2

4-hydroxy-2-methyl-N-(5-methyl-2-thiazolyl)-2H-1, 2-benzothiazine-3-carboxamide-1,1-dioxide (compound of Formula (II), polymorph I form of meloxicam 34.1 g (83.7 mmol) meloxicam potassium salt monohydrate are dissolved in the mixture of 1500 ml of 0.5% aqueous potassium hydroxide solution and 25 ml of ethanol at the temperature of 40-45° C. by stirring for 30 minutes. The yellow solution are added 2.0 g of activated carbon and after stirring for ten minutes, the carbon is filtered off. The filtrate are added 100 ml aqueous hydrochloric acid solution prepared by diluting 20 ml (23.6 g) concentrated hydrochloric acid to 100 ml final volume, at 30° C. in 30 minutes (pH 3-5). The suspension is stirred for two hours at 10° C. temperature, filtered and the product is washed on the filter with water.

Yield: 28.5 g (97.1% calculated on the basis of the weight of meloxicam potassium salt monohydrate as starting compound)

Melting point: 246-248° C.
Elemental analysis ($C_{14}H_{13}N_3O_4S_2$ (351.4)

| Calculated | C: 47.85 | H: 3.73 | N: 11.96 | S: 18.25 |
| Measured | C: 47.80 | H: 3.82 | N: 11.87 | S: 18.20 |

Purity (HPLC): 99.8%.

EXAMPLE 3

4-hydroxy-2-methyl-N-(5-methyl-2-thiazoyl)-2H-1, 2-benzothiazine-3-carboxamide-1,1-dioxide potassium salt monohydrate (compound of the Formula (I))

One proceeds according to Example 1 with the difference that instead of 4-hydroxy-2-methyl-2H-1,2-benzothiazine-3-carboxylic acid methylester [compound of the Formula (III), wherein R is methyl)], 36.83 g (130 mmol) 4-hydroxy-2-methyl-2H-1,2-benzothiazine-3-carboxylic acid ethylester [compound of the Formula (III), wherein R is ethyl] are used.

Yield: 46.9 g (88.5% calculated on the basis of the weight of the starting compound -hydroxy-2-methyl-2H-1,2-benzothiazine-3-carboxylic acid methylester of the Formula (III)).

Content (on the basis of potassium content): 99.6%
Water (Karl Fischer method): 4.7%
Elemental analysis [$C_{14}H_{12}KN_3O_4S_2.H_2O$ (407.5)]

| Calculated | C: 41.26 | H: 3.46 | N: 10.31 | S: 15.74 |
| Measured | C: 41.22 | H: 3.38 | N: 10.25 | S: 15.69 |

Purity (HPLC): 99.8%.

EXAMPLE 4

Meloxicam Polimorf I Form

One proceeds according to Example 2 with the only difference that the solution of the potassium salt is treated with 6.0 ml 96% acetic acid instead of hydrochloric acid.

Yield: 29.0 g (98.5% calculated on the basis of the amount of meloxicam potassium salt monohydrate of the Formula (I) used as starting compound).

Melting point: 246-248° C.
Elemental analysis ($C_{14}H_{13}N_3O_4S_2$ (351.4):

| Calculated | C: 47.85 | H: 3.73 | N: 11.96 | S: 18.25 |
| Measured | C: 47.89 | H: 3.68 | N: 11.91 | S: 18.29 |

Purity (HPLC) 99.8%.

What we claim is:

1. A process for the preparation of 99.8% pure 4-hydroxy-2-methyl-N-(5-methyl-2-thiazolyl)-2H-1,2-benzothiazine-3-carboxamide-1,1-dioxide (meloxicam) of the Formula (II)

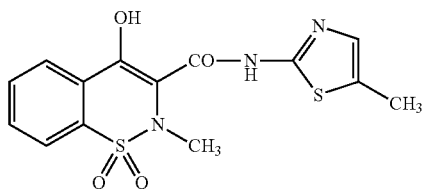

free of water-insoluble impurities of the compound of the Formula (V)

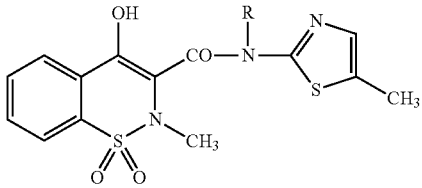

wherein R is methyl, ethyl or isopropyl, according to one of the following process variants:

(a) dissolving meloxicam potassium salt monohydrate of the Formula (I)

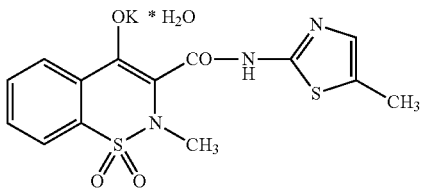

with the water-insoluble impurities of the Formula (V), in water or in a mixture of water and an organic solvent, removing from the meloxicam potassium salt monohydrate, the water-insoluble impurities of the compound of the Formula (V) and treating the resulting solution with an organic or inorganic acid, and crystallizing 99.8% pure meloxicam; or (b) transforming meloxicam raw product into crystalline meloxicam potassium salt monohydrate of the Formula (I) with the water-insoluble impurities of the compound of the Formula (V), dissolving said meloxicam potassium salt monohydrate of the Formula (I) with the water-insoluble impurities of the Formula (V) in water or in a mixture of water and an organic solvent, removing from the meloxicam potassium salt monohydrate, the water-insoluble impurities of the compound of the Formula (V), and treating the dissolved potassium salt of meloxicam with an organic or inorganic acid, followed by crystallization of 99.8% pure meloxicam of the Formula (II); or (c) (i) reacting a compound of the Formula (III)

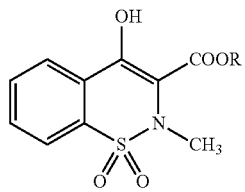

wherein R is methyl, ethyl or isopropyl with 2-amino-5-methyl-thiazole of the Formula (IV)

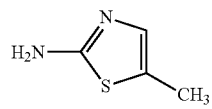

to form a meloxicam raw product of the Formula (II);
(ii) transforming the resulting meloxicam of the Formula (II) into its potassium monohydrate salt along with the water-insoluble impurities of the compound of the Formula (V),
(iii) separating the water-insoluble impurities of the compound of the Formula (V) from an aqueous or aqueous-organic solution of said meloxicam potassium salt to form a solution of 99.8% pure meloxicam; and
(iv) treating said solution with an organic or inorganic acid and crystallizing 99.8% pure meloxicam.

2. The process according to variants a), b) or c) defined in claim 1, wherein meloxicam potassium salt monohydrate of the Formula (I) is prepared by reacting meloxicam of the Formula (II) with potassium hydroxide or potassium carbonate dissolved in water or in the mixture of water and an organic solvent and if desired, crystallizing the meloxicam potassium salt monohydrate of the compound of the Formula (I) thus formed.

3. The process according to claim 2, wherein the molar amount of potassium hydroxide or potassium carbonate is 1-10 molar equivalents of the molar amount of meloxicam.

4. The process according to claim 1, wherein as organic solvent, an alcohol containing 1-4 carbon atoms is used.

5. The process according to variants (a), (b) or (c) of claim 2 wherein the acidic treatment of the solution of meloxicam potassium salt in water or in a mixture of water and an organic solvent is carried out by mixing said solution with an organic or inorganic acid.

6. The process according to claim 5, wherein the treatment of the solution of meloxicam potassium salt in water or in a mixture of water and an organic solvent with an acid is continued until reaching a pH of 3 to 6.

* * * * *